US006997862B2

(12) United States Patent
Terwilliger et al.

(10) Patent No.: US 6,997,862 B2
(45) Date of Patent: Feb. 14, 2006

(54) DELIVERY SYSTEM AND METHOD FOR INTERSTITIAL RADIATION THERAPY USING SEED STRANDS WITH CUSTOM END SPACING

(75) Inventors: Richard A. Terwilliger, Southbury, CT (US); Gary A. Lamoureux, Woodbury, CT (US)

(73) Assignee: IdeaMatrix, Inc., Estes Park, CO (US)

( * ) Notice: Subject to any disclaimer, the term of this patent is extended or adjusted under 35 U.S.C. 154(b) by 0 days.

(21) Appl. No.: 10/619,928

(22) Filed: Jul. 15, 2003

(65) Prior Publication Data

US 2004/0230087 A1    Nov. 18, 2004

Related U.S. Application Data

(60) Provisional application No. 60/469,940, filed on May 13, 2003.

(51) Int. Cl.
*A61M 36/00* (2006.01)
*A61N 5/00* (2006.01)
(52) U.S. Cl. .......................................... 600/8
(58) Field of Classification Search ............. 600/1–8, 600/426, 427; 60/439; 604/19, 57, 65, 116; 250/507.1, 506.1; 424/1.13, 422, 426, 1.61, 424/4.25; 514/411; 128/898; 29/401.1
See application file for complete search history.

(56) References Cited

U.S. PATENT DOCUMENTS

| | | | |
|---|---|---|---|
| 1,578,945 A | 3/1926 | Withers | |
| 2,067,589 A | 1/1937 | Antrim | |
| 3,351,049 A | 11/1967 | Lawrence | |
| 3,565,869 A | 2/1971 | De Prospero | |
| 3,636,956 A | 1/1972 | Schneider | |
| 4,052,988 A | 10/1977 | Doddi et al. | |
| 4,086,914 A | 5/1978 | Moore | |
| 4,167,179 A | 9/1979 | Kirsch | |
| 4,402,308 A | 9/1983 | Scott | |
| 4,509,506 A | 4/1985 | Windorski et al. | |
| 4,697,575 A | 10/1987 | Horowitz | |
| 4,754,745 A * | 7/1988 | Horowitz | 600/8 |
| 4,815,449 A * | 3/1989 | Horowitz | 600/7 |
| 5,460,592 A | 10/1995 | Langton et al. | |
| 5,713,828 A | 2/1998 | Coniglione | |
| 5,833,593 A | 11/1998 | Liprie | |
| 5,928,130 A * | 7/1999 | Schmidt | 600/7 |

(Continued)

FOREIGN PATENT DOCUMENTS

EP    030822    6/1981

OTHER PUBLICATIONS

U.S. Appl. No. 60/260,299, filed Feb. 26, 2002, Terwilliger et al.

(Continued)

*Primary Examiner*—Samuel G. Gilbert
(74) *Attorney, Agent, or Firm*—Fliesler Meyer LLP (57) ABSTRACT

A delivery system and method for interstitial radiation therapy comprising a substantially axially stiff and longitudinally flexible elongated strand made of material, which is bio-absorbable in living tissue and a plurality of radioactive seeds dispersed in a predetermined array within the strand. The delivery system and method further customize the strand based on a prescription. The strands can have custom end spacings, which allow the optimal placing of seeds within the treatment tissue by implanting a plurality of strands to the same depth. A plurality of these strands can be implanted at the same time by the use of a guiding device.

24 Claims, 5 Drawing Sheets

U.S. PATENT DOCUMENTS

| | | | |
|---|---|---|---|
| 5,938,583 A * | 8/1999 | Grimm | 600/7 |
| 6,010,446 A | 1/2000 | Grimm | |
| 6,039,684 A | 3/2000 | Ildstad et al. | |
| 6,080,099 A | 6/2000 | Slater et al. | |
| 6,132,677 A | 10/2000 | Ohriner | |
| 6,132,947 A | 10/2000 | Honam et al. | |
| 6,159,143 A | 12/2000 | Lennox | |
| 6,163,947 A | 12/2000 | Coniglione | |
| 6,200,255 B1 * | 3/2001 | Yu | 600/1 |
| 6,200,256 B1 | 3/2001 | Weinberger | |
| 6,248,057 B1 | 6/2001 | Mavity et al. | |
| 6,264,600 B1 | 7/2001 | Grimm | |
| 6,273,851 B1 * | 8/2001 | Slater et al. | 600/8 |
| 6,283,911 B1 | 9/2001 | Keren | |
| 6,312,374 B1 | 11/2001 | von Hoffmann | |
| 6,428,504 B1 * | 8/2002 | Riaziat et al. | 604/65 |
| 6,450,937 B1 * | 9/2002 | Mercereau et al. | 600/7 |
| 6,450,938 B1 * | 9/2002 | Miller | 600/7 |
| 6,450,939 B1 | 9/2002 | Grimm | |
| 6,497,646 B1 * | 12/2002 | Candelaria et al. | 600/7 |
| 6,500,109 B1 * | 12/2002 | Tokita et al. | 600/7 |
| 6,537,193 B1 | 3/2003 | Lennox | |
| 6,539,247 B1 * | 3/2003 | Spetz | 600/427 |
| 6,549,802 B1 * | 4/2003 | Thornton | 600/426 |
| 6,572,525 B1 * | 6/2003 | Yoshizumi | 600/7 |
| 6,626,817 B1 * | 9/2003 | Luth | 600/7 |
| 6,656,106 B1 * | 12/2003 | Schmidt | 600/7 |
| 6,752,753 B1 * | 6/2004 | Hoskins et al. | 600/7 |
| 2003/0191355 A1 * | 10/2003 | Ferguson | 600/3 |
| 2004/0015037 A1 * | 1/2004 | Rapach et al. | 600/1 |
| 2004/0158117 A1 * | 8/2004 | Drobnik et al. | 600/7 |
| 2004/0158118 A1 * | 8/2004 | Drobnik et al. | 600/8 |

OTHER PUBLICATIONS

Martines et al., "Sterilization of $^{125}$I Seed Encased in Vicryl Sutures for Permanet Interstitial Implantion", J. Rad. Onc. Bio. Phys. 5(3):411-413 (1979).

Van't Riet, "Ultrasonically Guided Transperineal Seed Implantation of the Prostate: Modification of the Technique and Qualitative Assessment of Implants", Intl. J. Rad. Onc. Biol. Phys. 24(3): 555-558 (1992).

Middleton et al., "Synthetic Biodegradable Polymers as Medical Devices", Med. Plas. Biomat. (Mar. 1998).

http://investor.mentorcorp.com/news/20010122-32414.cfm, "Mentor Acquires Breakthrough Brachytherapy Technology" (Jan. 25, 2002).

* cited by examiner

| Needle Number | Retraction (cm) | Hole Location | Number of Seeds |
|---|---|---|---|
| 1 | 1.00 | b4.0 | 3 |
| 2 | 0.00 | c4.0 | 5 |
| 3 | 0.00 | d4.0 | 5 |
| 4 | 1.00 | e4.0 | 3 |
| 5 | 1.50 | B3.5 | 3 |
| 6 | 0.50 | C3.5 | 5 |
| 7 | 0.50 | E3.5 | 5 |
| 8 | 1.50 | F3.5 | 3 |
| 9 | 2.00 | a3.0 | 2 |
| 10 | 1.00 | b3.0 | 4 |
| 11 | 0.00 | c3.0 | 2 |
| 12 | 0.00 | d3.0 | 2 |
| 13 | 1.00 | e3.0 | 4 |
| 14 | 2.00 | f3.0 | 2 |
| 15 | 1.50 | B2.5 | 3 |
| 16 | 0.50 | C2.5 | 2 |
| 17 | 0.50 | E2.5 | 2 |
| 18 | 1.50 | F2.5 | 3 |
| 19 | 2.00 | a2.0 | 2 |
| 20 | 1.00 | b2.0 | 4 |
| 21 | 0.00 | c2.0 | 3 |

DELIVERY SYSTEM AND METHOD FOR INTERSTITIAL RADIATION THERAPY USING SEED STRANDS WITH CUSTOM END SPACING

CLAIM OF PRIORITY

This application claims priority to U.S. Patent Provisional Application No. 60/469,940 filed May 13, 2003, which is incorporated herein by references.

CROSS-REFERENCE TO RELATED APPLICATIONS

The following applications are cross-referenced and incorporated herein in their entirety:

U.S. Patent Application No. 60/360,237, entitled "System for Manufacturing Interstitial Radiation Therapy Seed Strands", by Terwilliger et al., filed Feb. 26, 2002.

U.S. Patent Application No. 60/360,272 entitled "Delivery System and Method for Interstitial Radiation Therapy Using Strands Constructed with Extruded Strand Housing", by Terwilliger et al., filed Feb. 26, 2002.

U.S. patent application Ser. No. 10/162,548 entitled "Delivery System and Method for Interstitial Radiation Therapy Using Strands Constructed with Extruded Strand Housing", by Terwilliger et al., filed Jun. 4, 2002.

U.S. patent application Ser. No. 10/162,546 entitled, "System for Manufacturing Interstitial Radiation Therapy Seed Strands" by Terwilliger et al., filed Jun. 4, 2002.

U.S. patent application Ser. No. 10/162,006 entitled, Delivery System and Method for Interstitial Radiation Therapy Using Strands Constructed with Extruded Strand Housings", by Terwilliger et al., filed Jun. 4, 2002.

U.S. patent application Ser. No. 10/397,940 entitled, "Delivery System and Method for Interstitial Radiation Therapy" by Terwilliger et al., filed Mar. 26, 2003.

U.S. patent application Ser. No. 10/035,083 entitled, "Delivery System and Method for Interstitial Radiation Therapy" by Terwilliger et al., filed Dec. 28, 2001.

U.S. Patent Application No. 60/336,329 entitled, "Delivery System for Interstitial Radiation Therapy" by Terwilliger et al., filed Nov. 2, 2001.

FIELD OF THE INVENTION

The present invention relates to systems and methods for delivering a plurality of radioactive sources to a treatment site.

BACKGROUND

In interstitial radiation therapy, one method for treating tumors is to permanently place small, radioactive seeds into the tumor site. This method is currently accomplished by one of the following two procedures: (a) loose seeds are implanted in the target tissue, and/or (b) seeds are contained within a woven or braided absorbable carrier such as braided suture material and implanted in the target tissue. The loose seeds, however, are dependent on the tissue itself to hold each individual seed in place during treatment, and the woven or braided sutures do not assist in the placement of the seeds relative to the target tissue.

There have been many developments in brachytherapy (i.e., therapy relating to treating malignant tumors for handling such radioactive seeds). In one technique, hollow metal needles are inserted into the tumor and the seeds are thereafter inserted into the needles, while the needles are being retracted to deposit the seeds in the tumor. Such devices are shown in U.S. Pat. No. 4,402,308, which is incorporated herein by reference. The most commonly used instruments are the Henschke and Mick devices. The use of such devices has distinct disadvantages. The overall length of such devices is over 20 inches and such devices have significant weight making them difficult to manipulate.

Another disadvantage of the above technique is that the seeds are deposited in a track made by the needle. When the needle is withdrawn, there is a tendency for the seeds to migrate in that track resulting in a poor distribution of the seeds. Because the energy levels are low, distribution between centers of adjacent seeds should be on the order of about 1 cm for certain treatments. Poor distribution of seeds can result in undesirable concentrations of seeds resulting in either an over-dosage or under-dosage of radiation. Further, over time, the seeds tend to migrate along the needle track, away from the tumor, and accordingly patients commonly must repeat the procedure within a couple months to have seeds re-implanted near the tumor.

Further complicating the procedure is the fact that the seeds are small, because they need to fit in small bore needles to prevent excessive tissue damage. Due to their small size and high seed surface dose, the seeds are difficult to handle and to label, and can easily be lost. In addition, the technique of implantation of individual seeds is time consuming.

One preferred method of introducing seeds into the tumor site is using a pre-manufactured elongated assembly or implant that contains seeds spaced at 1 cm increments. This assembly is capable of being loaded into an introducer needle just prior to the procedure. What is desired in using an elongated assembly of seeds and spacers is the ability to insert such an assembly into a tumor site to provide controlled and precise placement of the radioactive seeds.

While assemblies with bio-absorbable materials and spaced radioactive seeds are known for use as interstitial implants, such assemblies are not entirely satisfactory. In one instance, the elongated implant is made using a bio-absorbable material consisting of an Ethicon Vicryl.RTM. This material is commonly known as PGA. Radioactive seeds and teflon spacers are inserted into the material. The carrier is heated causing contraction of the carrier material and resulting in a rigid column of seeds and spacers. This technique was reported in "Ultrasonically Guided Transperineal Seed Implantation of the Prostate: Modification of the Technique and Qualitative Assessment of Implants" by Van't Riet, et al., *International Journal of Radiation Oncology, Biology and Physics*, Vol. 24, No. 3, pp. 555–558, 1992 which is incorporated herein by reference. Such rigid implants have many drawbacks, including not having the ability to flex with the tissue over the time that the bio-absorbable material dissolves.

As the tissue or glands shrink back to pre-operative size, and thus as the tissue recedes, a rigid elongated implant does not move with the tissue, but remains stationary relative to the patient. The final location relative to the tumor is thus not maintained and the dosage of the radioactive seeds does not meet the preoperative therapy plan.

Another system for providing an elongated implant having radioactive seeds disposed therein is disclosed in U.S. Pat. No. 4,697,575, which is incorporated herein by reference. In this reference, a plurality of encapsulated radioactive seeds are positioned in a predetermined array. The seeds are encapsulated in individual capsules, with each capsule having a projection on one capsule end and a complementary recess on the remaining capsule end. A projection in one capsule is engageable with a recess in an adjacent capsule such that the desired number of seeds can be plugged together to form a column of rigid, bio-absorbable and elongated material. This implant is not entirely satisfactory inasmuch as it is time consuming and inefficient to carry out the manipulative steps of assembling such a strand of elongated material. Further, the implant is quite rigid as it is inserted into a patient without the use of an introduction needle, as the implant itself acts as a rigid needle that is undesirably left in place.

In another embodiment disclosed in the above patent, a rigid implant containing radioactive segments, with break points, is inserted into the tumor. The implant is made of a bio-absorbable polymer that is rigid enough to be driven into the tumor without deflection and without the use of a separate hollow needle. When the proper depth is reached with the rigid polymer needle, the remaining, uninserted portion of the needle is broken off. This embodiment has the disadvantage of the above embodiment, in that being too rigid, the implant does not follow the tumor as it shrinks back to its normal size.

In U.S. Pat. No. 6,163,947, Coniglione, issued Dec. 26, 2000, and incorporated herein by reference, a string of hollow seeds described in U.S. Pat. No. 5,713,828, issued Feb. 3, 1998, also incorporated herein by reference, are strung onto a thin strand of suture material to form an array of seeds. This string of seeds is delivered into the tumor site placed within a hollow needle. Since the hollow lumen of the seeds are substantially smaller in diameter in relation to the outside diameter of the seed body, the string of suture material must be substantially smaller in diameter than the seeds themselves. The resulting diameter of the suture makes the suture axially weak and the suture can fold up between the seeds within the needle lumen as pressure is applied on the proximal end of the strand within the needle. Thus the difference in diameter between the seed and the thin suture material makes the assembly susceptible to collapse from axial force applied on the proximal end, resulting in jamming of the assembly within the needle lumen and/or the assembly not maintaining the proper desired spacing between radioactive seeds as the assembly is expelled into the treatment site.

One relevant reference discloses modification of the needle structure to include a reloadable cartridge. In such reference, the needle is inserted and as a cartridge of seeds is emptied, the plunger of the device is withdrawn and a new cartridge containing radioactive seeds is loaded into the syringe (Moore, U.S. Pat. No. 4,086,914, issued May 2, 1978). Another reference offers a device for implanting individual seeds in a planar dispensing device with multiple needles to ensure accurate placement of the seeds relative to one another and the treatment site (Kirsch, U.S. Pat. No. 4,167,179, issued Sep. 11, 1979). Another reference disclosed a shielding devices for bead strands which prevents radiation exposure for health care personnel performing treatment with the radioactive seeds (Windarski, U.S. Pat. No. 4,509,506 issued Apr. 9, 1985). All of the above references are incorporated herein by reference.

In another technique for treating tumors disclosed in U.S. Pat. No. 5,460,592, and incorporated herein by reference, seeds are held in a woven or braided bio-absorbable carrier such as a braided suture. The carrier with the seeds laced therein is then secured in place to form a suitable implant. This braided assembly exhibits many drawbacks, such as when the braided assembly is placed into the tumor. The needle that carries the braided assembly must be blocked at the distal end to prevent body fluids from entering the lumen. If body fluid reaches the braided assembly while the assembly is still in the lumen of the needle, the braided assembly can swell and jam in the lumen. Because the assembly is made of a braided tubular material, it is difficult to push the assembly out of the needle. As the needle is withdrawn from the tumor, pressure on the proximal end of the braided assembly causes the braid to expand and jam inside the lumen of the needle. Finally, if the braided strand is successfully expelled from the needle, the relative spacing of the seeds may not be maintained, if the braided material has collapsed.

Other references that address such implants and materials include the following, all of which are incorporated herein by reference.

1. U.S. Pat. No. 1,578,945, issued January 1923 to Withers;
2. U.S. Pat. No. 2,067,589, issued January 1937 to Antrim;
3. U.S. Pat. No. 3,351,049, issued November 1967 to Lawrence;
4. Medi-Physics brochure entitled AI-125 Seeds.RTM. In Carrier,@ Model No. 6720;
5. Medi-Physics brochure entitled Al-125 Seed.RTM. Source Model 6711;" and
6. Martinez et al., *Int. J Radiation Oncology Biol. Phys.*, Vol. 5, No. 3, March 1979, pp. 411–413.

SUMMARY OF SOME ASPECTS OF THE INVENTION

Accordingly, the present invention cures and addresses the disadvantages exhibited in the prior art devices and implants. What is desired is to provide a bio-absorbable carrier material having seeds disposed within the material, with the seeds being accurately spaced a predetermined distance from one another, and with the seeds repeatably maintaining that spacing, even after being introduced into the body.

It is also desired that an elongated member with seeds be sufficiently rigid axially to allow expulsion of the member while maintaining the spacing between seeds, and that the member be flexible and pliable enough to move with the tissue as the tissue shrinks back to pre-operative size.

In a further aspect, an embodiment of the invention has an end spacing configured to match the relative distance the needle needs to be retracted after the initial insertion in order to position the needle relative to a site, eliminating retraction prior to seed placement, and allowing all needles to be inserted to the same depth in the patient, thus reducing implant time.

It is further desired to shorten the time required for the preparation and implantation of a plurality of these elongated members.

Accordingly, some of the objectives of the present invention include providing an elongated member with seeds dispersed throughout, which obviates the aforementioned disadvantages and allows placement of the seeds in accurate positions to provide the desired interstitial radiation dose to the location derived from a preoperative dosimeter plan.

A further object of the present invention is to provide a delivery system for interstitial radiation therapy, which is faster and easier to use than prior art systems.

Another object of the present invention is a delivery system that causes a minimum of trauma to tissue.

A related object is to have the ability to implant a plurality of these delivery systems at the same time.

Yet, another object of the present invention is a delivery system that allows for control of the radiation dosage given the tissue. Still further objects of the present invention are a delivery system that can be used and placed with precision, and that maintains the position of the implant after the implantation, until the bio-compatible material dissolves and the seeds have become inert. In another aspect, the bio-compatible material is selected to absorb about when the half-life of the radioactive seeds is reached.

A further aspect is to have the implant be echogenic.

In accordance with an embodiment of the invention, the delivery system comprises a substantially axially stiff and longitudinally flexible elongated member that is bio-absorbable in living tissue. The member has a length that greatly exceeds its width or diameter. The elongated member has a plurality of radioactive seeds dispersed therein in a predetermined array.

In another embodiment, the substantially axially stiff and longitudinally flexible elongated member comprises a single continuous monofilament element of bio-compatible material that has a plurality of seed sources molded therein. The bio-compatible material can be preferably a bio-absorbable polymer or copolymer material that encapsulates the plurality of radioactive seeds.

A further embodiment of the invention is characterized as a substantially constant diameter solid elongated matrix member of a bio-absorbable polymer with seeds positioned therein at predetermined spacing along its length, whose diameter is a close fit to the needle lumen, thus preventing collapse as axial force is applied on the proximal end of the elongated matrix member. The space between the seed sources is maintained throughout the insertion and expulsion of the elongated matrix member. The diameter of the polymer between the seeds may be slightly reduced in diameter in relation to the overall diameter of the elongated matrix member, but is of sufficient diameter so as to not allow collapse of the matrix member within the needle lumen.

The present embodiment of the invention further allows for variation in any spacing between seeds, as the semi-rigid, deflecting elongate member could be produced under a doctor's prescription for each patient, with optimal seed distribution for a particular patients treatment program.

This one object of the invention is to provide an implant that can be custom made as specified by a prescription for an individual patient.

A related object is to provide a plurality of implants that can be easily implanted at the same time.

Further aspects, objects, advantage and embodiment of the invention can be understood from the specification, the figures and the claims.

DETAILED DESCRIPTION OF THE PREFERRED EMBODIMENTS

In accordance with an embodiment of the invention, a substantially axially, semi-rigid and longitudinally flexible elongated member made of material, which is bio-absorbable in living tissue, is provided for insertion in tumors. A plurality of radioactive seeds are encapsulated and positioned in a predetermined array in the member in the desired spaced relationships.

The seeds can be of various types having low energy and low half-life such as Iodine seeds, known as I-125 seeds, consisting of a welded titanium capsule containing iodine 125 absorbed on a silver rod, or Palladium 103 seeds. Examples of radioactive seeds used to manufacture the therapeutic element appear in Table 1 below.

TABLE 1

Seed Manufacturers and Common Types of Seeds.

| PART NUMBER | MANUFACTURER | SEED NAME |
|---|---|---|
| IODINE$^{125}$ | | |
| 80040-A | Amersham 6702 | OncoSeed |
| 80040-B | Amersham 6711 | RAPID Strand |
| 80040-C | North American Scientific | IoGold |
| 80040-D | Best Industries | BEST Iodine-125 |
| 80040-E | Bebig | Symmetra |
| 80040-F | Mills Biopharmaceuticals | ProstaSeed |
| 80040-G | Syncor | PharmaSeed |
| 80040-H | International Isotopes | IsoStar |
| 80040-I | Implant Sciences | I-Plant |
| 80040-J | International Brachytherapy | InterSource-125 |
| 80040-K | Source Tech | STM1251 |
| 80040-L | DRAXIMAGE, Inc. | BrachySeed |
| PALLADIUM$^{103}$ | | |
| 80035-A | North American Scientific | Pd Gold |
| 80035-B | Theragenics | Theraseed 200 |
| 80035-C | Best Industries | BEST Palladium-103 |
| 80035-D | International Brachytherapy | InterSource 103 |

Additionally, seeds can be manufactured using iridium 192, cesium 131, gold 198, yttrium 90 and phosphorus 32. Further radioactive isotopes used to manufacture seeds are not limited to these examples, but can include other sources of different types of radiation. In addition, it is to be understood that other types of seeds can be used. In particular, seeds such as those described in U.S. Pat. No. 6,248,057, which patent is incorporated herein by reference and which is entitled "Absorbable Brachytherapy and Chemotherapy Delivery Devices and Methods", can be used with the present invention. These seeds include radiation delivery devices, drug delivery devices, and combinations of radiation and drug delivery devices in the form of beads, seeds, particles, rods, gels, and the like. These particular seeds are absorbable wherein the radiation element or drug delivery element is contained within, for example, absorbable polymers such as those listed below or in the above-referenced patent. In such seeds, the bio-absorbable structure can have a predefined persistence, which is the same as or substantially longer than a half-life of the radioactive element contained in the bio-absorbable structure. These above bio-absorbable seeds can be used in the same manner as the seeds described herein with respect to the invention.

The substantially axially, semi-rigid, and longitudinally flexible elongated member may be made of any of the natural and/or synthetic bio-compatible and bio-absorbable materials. Natural and synthetic polymers and copolymers can be used. Examples of synthetic bio-absorbable polymer materials are the polymers and copolymers of glycolide and lactide, polydioxanone and the like. Such polymeric materials are more fully described in U.S. Pat. Nos. 3,565,869; 3,636,956; 4,052,988 and European Patent Application No. 30822, all of which are incorporated herein by reference. Specific examples of bio-absorbable polymeric materials that can be used to produce the substantially axially stiff and longitudinally flexible elongated member of an embodiment of the present invention are polymers made by ETHICON, Inc., Somerville, N.J., under the trademarks "MONOCRYL" and "MAXON," which material is incorporated herein by reference.

Table 2 below provides examples of polymers (and manufacturers) suitable for use in producing embodiments the therapeutic member of the invention. A further discussion of such biodegradable polymers can be found in an article by John C. Middleton and Arthur J. Tipton entitled "Synthetic Biodegradable Polymers as Medical Devices", published March 1998 in *Medical Plastics and Bio-materials*, which article is incorporated herein by reference.

TABLE 2

Biodegradable polymers, properties and degradation time.

| POLYMER | MELTING POINT (° C.) | GLASS-TRANSITION TEMP (° C.) | MODULUS (Gpa)[a] | DEGRADATION TIME (MONTHS)[b] |
|---|---|---|---|---|
| PGA | 225–230 | 35–40 | 7.0 | 6 to 12 |
| LPLA | 173–178 | 60–65 | 2.7 | >24 |
| DLPLA | Amorphous | 55–60 | 1.9 | 12 to 16 |
| PCL | 58–63 | (−65)–(−60) | 0.4 | >24 |
| PDO | N/A | (−10)–0 | 1.5 | 6 to 12 |
| PGA-TMC | N/A | N/A | 2.4 | 6 to 12 |
| 85/15 DLPLG | Amorphous | 50–55 | 2.0 | 5 to 6 |
| 75/25 DLPLG | Amorphous | 50–55 | 2.0 | 4 to 5 |
| 65/35 DLPLG | Amorphous | 45–50 | 2.0 | 3 to 4 |
| 50/50 DLPLG | Amorphous | 45–50 | 2.0 | 1 to 2 |

[a]Tensile or flexural modulus.
[b]Time to complete mass loss. Rate also depends on part geometry.

The final hardness of the polymer of elongate member should preferably be in a range from 20 to 80 durometers, and, more preferably, in the range of 20–40 durometers. The bio-absorbable material should preferably be absorbed in living tissue in a period of time of from about 70 to about 120 days, but can be manufactured to be absorbed anywhere in a range from 1 week to 1 year, depending on the therapeutic plan for each specific patient. Preferably, the bio-absorbable material is selected to absorb about when the half-life of the radioactive seeds is reached.

The member or strand is fashioned with a manufacturing method known as insert or compression molding. The radioactive seeds are placed into a fixture that spaces the seeds at the appropriate intervals in a cavity that is shaped to the desired final dimensions of the elongated member. All the spacings can be of different lengths, if the preoperative therapeutic plan so specifies. The synthetic polymer is introduced into the mold at a temperature that is above the melt point of the polymer. The polymer flows around the seeds within the cavity, surrounds the seeds and fills in the spaces between the seeds. After the mold has cooled, it is disassembled, and the finished elongated member is removed. Because the polymer flows at temperatures significantly greater than 250° F., the therapeutic element can easily be steam sterilized before implantation.

As specified above, the elongated member encapsulating radioactive seeds may be fashioned using compression molding techniques. Compression molding forms the molded piece in a two part mold where the polymer material is placed within the cavities of the mold in a liquid state. The seeds are placed in position within the cavities filled with the polymer and the mold is closed and compressed, then cooled to form a piece that conforms to the shape of the closed cavity.

The manufacturing process also can make the member echogenic. In the case of the molding of the elongated member, air can be entrapped in the polymer material. During the cooling stage of the molding process, the mold is placed in a vacuum chamber and the air in the chamber is evacuated. This causes the entrapped air in the mold to come out of solution from the polymer, and as the mold cools, this air is entrapped within the cooling polymer in the form of minute bubbles suspended in the plastic.

Air is a strong reflector of ultrasound energy, since the inherent impedance of air is many times greater than body tissue. When the elongated member is introduced into the body and imaged with ultrasound, the elongated member is clearly visible in the resulting image, and is, thus, echogenic.

The resulting elongated member is now a single solid monofilament of the polymer with the seeds spaced within the monofilament and encapsulated at the appropriate intervals. The member is generally very axially flexible such that it can be bent back upon itself in a circle without kinking. However, the member has sufficient column strength along its longitudinal axis so that the member can be urged out of a hollow needle without the member folding upon itself. Again, the intervals can be selected to be any distance or combination of distances that are optimal for the treatment plan of the patient.

Figure 1:
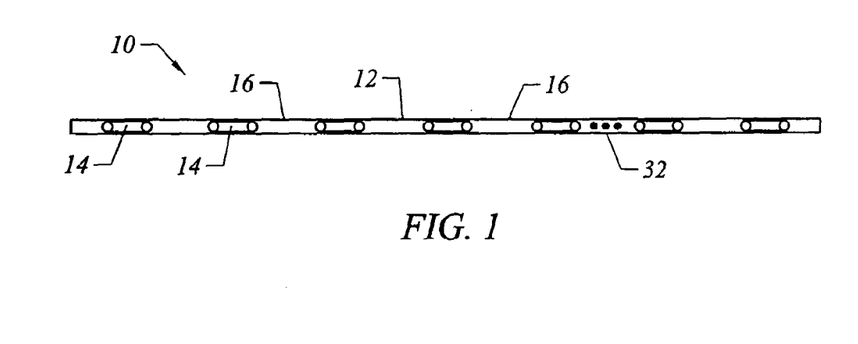
FIG. 1 is an enlarged side view of an embodiment of the therapeutic implant of the invention.
Figure 2:
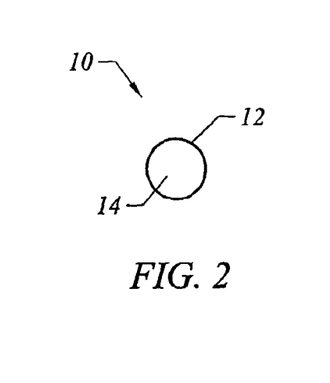
FIG. 2 is an enlarged view of a cross section of an embodiment of the therapeutic implant of the invention of FIG. 1.

In FIG. 1, the therapeutic elongated element, member or matrix or strand 10 is displayed having the semi-rigid, radially flexible polymer 12 and the radioactive seeds 14. As can be seen in FIG. 1, the polymer fills the spacing segments 16 in a contiguous manner to fashion the total elongate member.

Figure 3:
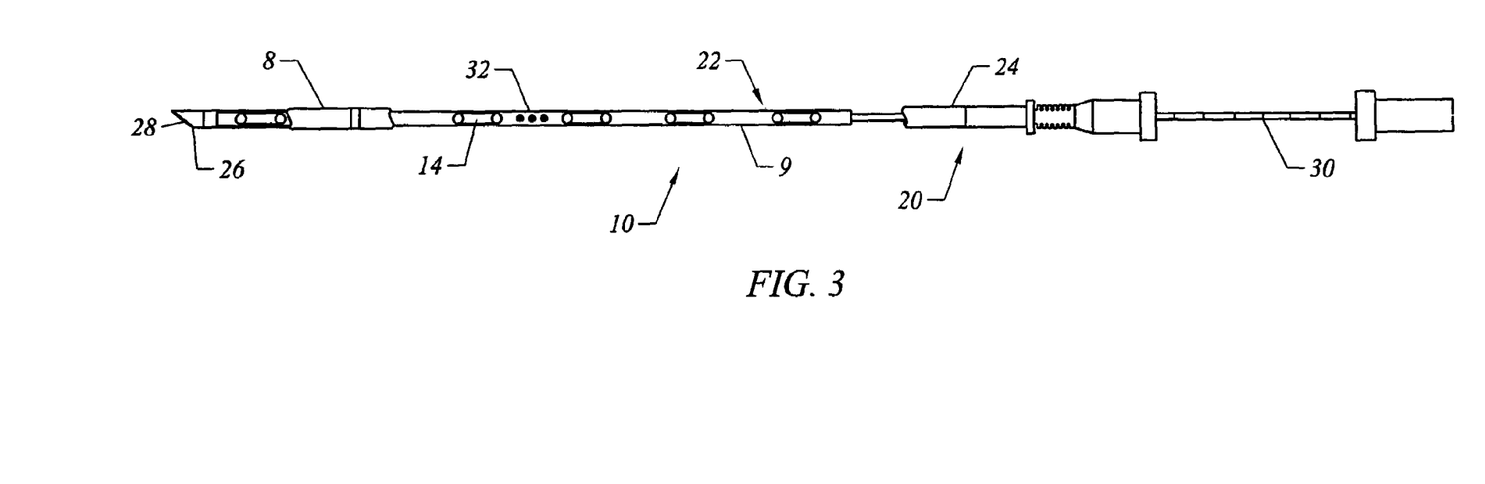
FIG. 3 is an enlarged side view of the brachytherapy device including the implant of FIG. 1.

FIG. 3 shows a side view of the brachytherapy device 20. The needle 22 is shown partially broken away and has a sheath component 24, and is loaded with the therapeutic element or member 10. The beveled end 26 of the needle 22 is plugged with a bio-compatible substance 28. The plug prevents fluids and tissue from entering the needle and coming in contact with the member 10 prior to the placement of the member or strand 10 adjacent the tumor. The plug 28 can be made out of a bone wax or can be made of one of the bio-absorbable polymers or copolymers listed herein. Further, the plug can be the end of the member or strand 10 that is heated and reflowed after the strand or member is inserted into the needle. A stylet or stylus 30 is inserted into the needle until it meets the therapeutic element or member 10. Then, the needle 22 is inserted into the site and the therapeutic member 10 is gradually extruded from the needle via the static force of the stationary stylus 30, as the needle 22 is pulled back.

Based on the above, it is evident that the present invention provides for an embodiment having an elongated member, which is comprised of a biodegradable polymer, which encapsulates a plurality of spaced radioactive therapeutic seeds. The seeds can be spaced in custom manner so that each member or strand is designed for the particular patient. That is to say that the spacing between each seed pair in a strand or member can be different for each seed pair. Further, each individual strand can have an entirely different seed spacing pattern than the next strand or member. Characteristically, or typically, for a surgical procedure, up to twenty-five of such strands or members are used to encircle the organ or tumor that is affected.

Further, such an arrangement provides for a strand or member that is stiff along its longitudinal axis. That is to say that the strand or member has column strength or stiffness while the strand or member is flexible in the direction which is radial or substantially perpendicular to the longitudinal axis. Accordingly, the strand or member in a preferred embodiment is able to bend back upon and touch itself, when formed in a characteristic length.

In other embodiments, the strand or member can be made with the incorporation of drugs and/or hormones and/or other therapeutics, which are embedded in or formed in the polymer and/or seeds. Thus, the embodiment of the invention can deliver not only radioactive seeds, but such therapeutic drugs, hormones and other therapeutic devices. In addition, the strand or member can deliver heated seeds such as provided by ATI Medical of San Diego, Calif. These seeds can be preferably heated to from about six (6) degrees centigrade to about seventy (70) degrees centigrade after being inserted into a patient in a preferred embodiment.

It should be understood that other seed types can be used with the present invention. Thus, for example, in addition to the above encapsulated seeds, seeds which are made of radioactive or coiled wires can be embedded in the polymer and be within the spirit and scope of the invention. These seeds can be individual seeds, which are spaced within a polymer, or a continuous seed which extends the length of the strand or member.

Further to the invention, as discussed above, it should be understood that the strand or member can be made echogenic by the incorporation of, for example, air bubbles 32 in the polymer spaces between the seeds, as can be seen in FIGS. 1 and 3. These air bubbles or pockets can be formed in the polymer in ways identified above and other ways known to one of skill in the art.

According to the above, the advantages of the improved delivery system submitted of the present invention are:
1. The substantially axially stiff and longitudinally flexible elongated member allows controlled placement of the plurality of radioactive seeds that are encapsulated and positioned in a predetermined array in the member without migration of the individual radioactive seeds during the time the seeds are treating the tumor.
2. The fixed linear positioning of the seeds minimizes "hot" and "cold" radiation spots due to undesirable movement of the seeds.
3. The normal tissue is spaced away from the seed surface by the thickness of the body of polymer, to decrease necrosis from a high local dose.
4. The axial stiffness of the elongated member allows the elongated member to be urged out of the needle as the needle is withdrawn, without the member jamming in the needle, by collapsing or expanding as the needle is withdrawn from the tumor site.
5. The longitudinal flexibility of the elongated member allows locational accuracy to be maintained as the gland shrinks to pre-procedural size, as the swelling that occurs during tissue disruption and needle manipulation recedes.
6. Increased speed of implant resulting in reduced surgical time and health care provider radiation exposure.

Method of Delivering Customized Strands and/or Members Per a Therapeutic Prescription:

As is known in the industry, there is software which can be used to provide brachytherapy treatment planning guides which are customized for each individual patient. Such software is provided by Rossmed, which is located at Ross Medical, 7100, Columbia Gateway Drive, Suite 160, Columbia, Md. 21046. This particular software, which is incorporated herein by reference, is known as the Strata suite, which software helps physicians to develop and visualize low dose rate brachytherapy treatment plans for treating malignant tumors in human tissue. The treatments entail the use of radioactive seed sources, which are implanted adjacent to the malignant tissue. The Strata software uses imaging to create a three-dimensional reconstruction of the patient's anatomy. The software is able to plan the placement of the seeds within the target. The radiation dose that is delivered to the target can be computerized and visualized using the software. The software can then specify an optimal number of strands or members along with optimal seed dosages and spaces between seeds. At times, the loading plans so specified cannot be optimized by the physician in preparing the seed and spacer loads for the needles, as the spacers come in only predefined lengths.

Accordingly, with the present invention, the software can be used to prepare a prescription, which optimizes the number of members or strands, and placement and spacing of seeds for each of the strands or members. This optimization plan can then be sent to a manufacturing site. By using the techniques of an embodiment of the present invention, an optimized strand or member can be created with the specified number of seeds and the specified distances between each seed pair. Once this prescription is filled at the manufacturing site, the custom strand or member can be sent back to the physician for treatment of the patient. With such an arrangement, radiation patterns can be optimally established for the treatment of each patient. Further, the preparation time for the physician is greatly diminished as the physician does not have to hand assemble and hand load the seeds and spacers into the needle.

By using the diagnosis software to obtain precise dimensions of the target tumor or tissue, each individual strand can be custom-manufactured in such a way that the placement of seeds coincides with the target tissue precisely, while maintaining the same depth of implantation for a plurality of strands. All a physician has to do is to implant each strand in its designated spot to the same depth (for example, all strands would be implanted flush again a tissue surface), and the seeds will be placed correctly within the treatment tissue. (In other words, no seeds will protrude beyond the boundaries of the treatment tissue.)

Improved Implantation Method and Seed Strands

Figure 4A:
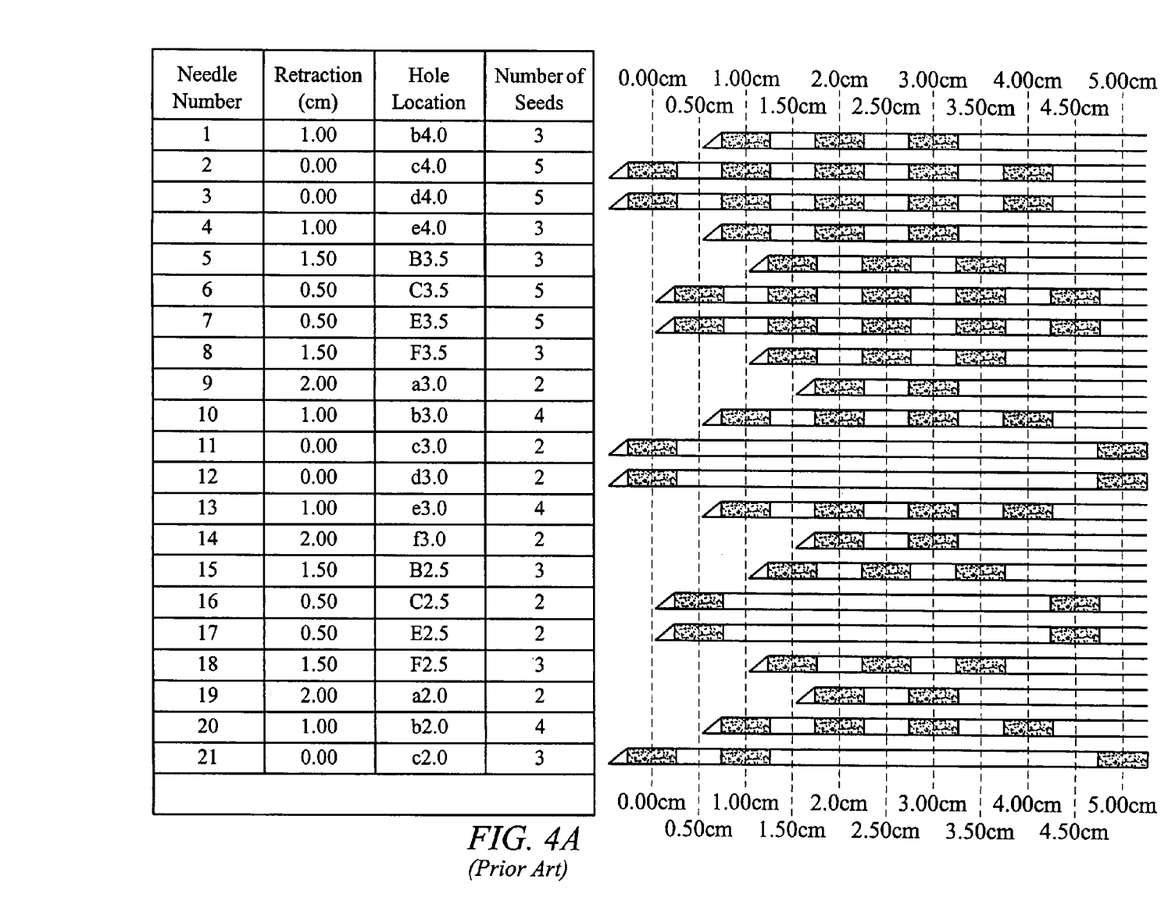
FIG. 4A shows a plurality of strand implants in accordance with the prior art.

As is known to the practitioner, generally prior art seed strands come in a fixed length. To correctly place each seed at its designated spot, previous methods required injecting hollow needles into the tissue and then retracting each needle by a certain amount before the strands can be implanted at the correct depth. FIG. 4A shows an exemplary pre-operative diagnostic plan created by the methods and software discussed above. Each strand 401, 402, 403 and so on can have a different number of seeds and spacing between the seeds, and each strand typically have a seed proximate to the distal, or pointed, end. Needles numbered 1 through 21 in this example are urged fully into a fixed depth designated as 0.00 cm, and then retracted as needed. Needle #1, for example, is retracted 1.00 cm before the seed strand is implanted into the tissue. For needle #2, the needle need not be retracted before implantation because a seed is to be deposited at the 0.00 cm depth. For Needle #5, the retraction distance is 1.50 cm, and so on. We can see each needle can have a different retraction amount, making the implantation operation cumbersome and time-consuming. It is quite naturally desirable to provide a method and seed strand that can overcome this disadvantageous process.

Figure 4B:
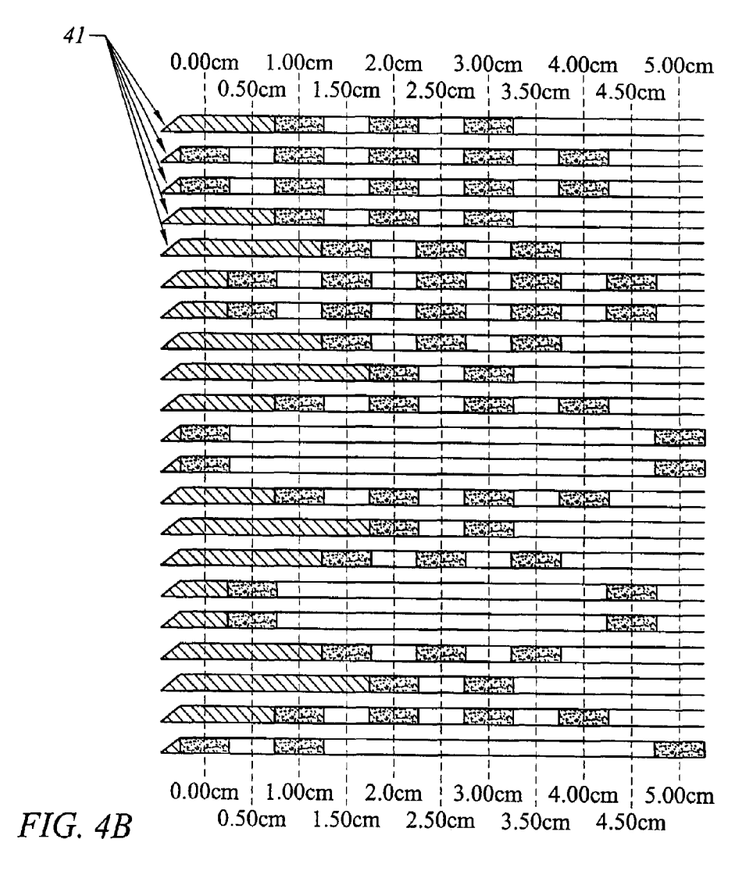
FIG. 4B depicts a plurality of strand implants of an embodiment of the invention with custom end spaces at the distal end of selected strand implants.

Refer to FIG. 4B, the present embodiments of the invention provide for custom seed strands and a method to significantly shorten the implantation time. The strands are of substantially uniform length, but with distal ends 41 of individual strands having customized end spacers so that the physician can implant each strand to the same depth. In the diagrams, the distal ends are shaded only for clarity. In a preferred embodiment of the invention, the distal ends could be made of the same polymeric material as the strand body. The spacings between the seeds, and the custom distal end spacing are provided in the strand in accordance with the methods presented above.

With the use of these novel implants, the physician need not be concerned about the depth of the implant as each needle is urged into the patient to the same depth and each strand would be implanted at that depth as the needle is pulled back leaving the strand in place. There is no need to identify the distal end of each strand by ultrasound or visual inspection, or to specially position each strand to a custom depth. There is no concern or need to retract a needle before implanting any strand. Accordingly, the elapse time for the surgical procedure is shortened with less exposure of the physician to the strand and less time that the patient must endure the procedure.

According to the invention, the strands are implanted into the patient according to a location map and an implantation plan. Each strand is implanted to the same depth. The implantation map can be marked onto the patent or can be applied to a pliable material that is laid over the implant site. Implantation can also occur without such a map and in accordance to an implantation plan.

Figure 5A:
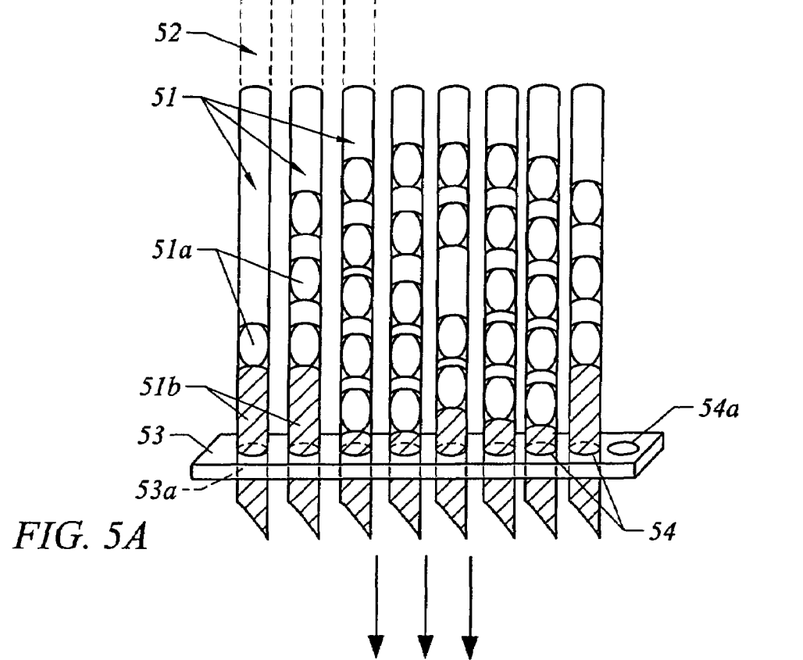
FIG. 5A depicts needles containing strands of embodiments of the invention aligned with a template.

Another embodiment of the invention uses an exemplary device or template 53 as discussed below and as depicted in FIG. 5A. FIG. 5A shows an embodiment of the invention, which allows for multiple implantations of strands at once. A plurality of treatment strands according to the invention 51 (as loaded into implantation needles 52, not shown) can be aligned and held in place by an exemplary device 53 that has a plurality of receptacles 54 for the needles to pass through. Each custom-made strand, with custom-spaced seeds 51a and custom distal ends 51b (shaded in the diagram), is loaded into its individually designated receptacle. Note that it may not be necessary to load all receptacles with a strand (see unloaded receptacle 44a) if the tumor to be treated is small in size.

Figure 5B:
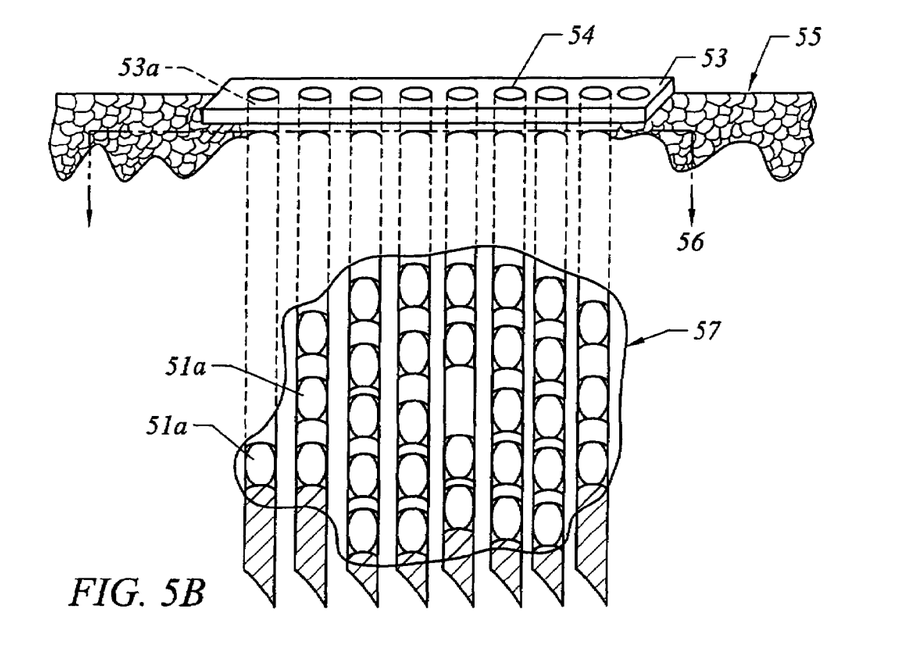
FIG. 5B depicts the template of FIG. 5A with the custom strand implants positioned in the tissue of the patient.

Next, the template, having a substantially flat surface 53a on the bottom side, is maneuvered and positioned onto a tissue surface 55 of the patient FIG. 5B. Said tissue surface 55 may be an outer epidermis of the patient if the procedure is non-surgical, or an inner dermis if the procedure is surgical. After the device is positioned, all the loaded strands can be implanted at the same time to the same depth 56. As each needle is removed, the strand is left in place. As each strand has a custom spacer end there is no need for the physicians to withdraw any needle a specific amount as taught by the prior art, prior to the strand being dispensed from the needle. Accordingly, time is conserved during the implantation procedure. Once the strands are implanted, all the seeds will be properly aligned according to the pre-operative treatment plan. The template is then removed.

By using the template as a guide and the customized strands, the treating physician does not have to be concerned about variations in the implantation depth of each implant. Further, if multiple needles are injected at once, this method can substantially reduce the time needed for the procedure.

Figure 5C:
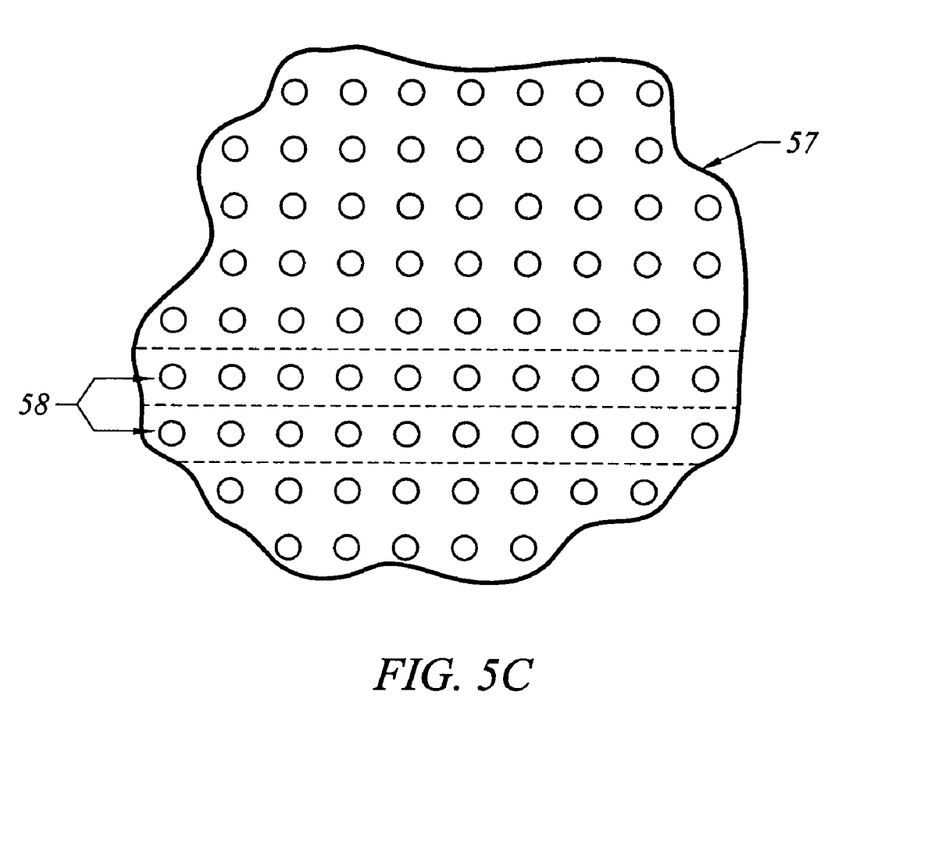
FIG. 5C depicts a top view of the embodiment of the invention as depicted in FIG. 5B.

Subsequent rows of implants can be implanted by repeating the procedure outlined above. See FIG. 5C, which depicts a top view of the same tumor depicted in FIG. 5B, showing rows 58 of implants implanted by the procedure. In another embodiment, the template may have multiple rows, allowing for an even greater number of implants at once.

Additional aspects, objects and advantages of the invention can be obtained through a review of the appendant claims and figures. It is to be understood that other embodiments can be fabricated and come within the spirit and scope of the claims and the invention.

The foregoing description of preferred embodiments of the present invention has been provided for the purposes of illustration and description. It is not intended to be exhaustive or to limit the invention to the precise forms disclosed. Many modifications and variations will be apparent to one of ordinary skill in the relevant arts. It is intended that the scope of the invention be defined by the claims and their equivalence.

What is claimed is:

1. A prescription method to create a plurality of treatment strands, comprising:
   accepting a tissue treatment plan for the tissue to be treated, which treatment plan specifies a number and spacing of treatment seeds to be provided in each of a plurality of treatment strands that includes a distal end and a proximal end, where the distal end is intended to be implanted prior to the proximal end; and
   creating the plurality of treatment strands so that the treatment strands satisfy the treatment plan when distal ends of the treatment strands are implanted into a patient to the same depth using needles that are inserted into the patient to the same depth;
   wherein at least two of the plurality of treatment strands have a custom distal end spacing between the distal end of each treatment strand and the adjacent treatment seed to thereby enable the treatment plan to be satisfied when the distal ends of the plurality of the treatment strands are implanted to the same depth using needles that are inserted to the same depth; and
   wherein the custom distal end spacings of at least two of the plurality of the treatment strands have different lengths.

2. The method of claim 1, wherein:
   said step of creating the plurality of treatment strands includes positioning radioactive seeds in a mold and introducing into the mold a material to mold the radioactive seeds in place.

3. The method of claim 2, wherein the material introduced into the mold is bio-absorbable.

4. The method of claim 2, wherein the material introduced into the mold is a polymer.

5. The method of claim 1, further comprising:
   aligning the created plurality of treatment strands in a template.

6. The method of claim 5, wherein all of the plurality of created treatment strands are the same length.

7. A prescription method to create a plurality of treatment seed strands for treating tissue, comprising:

accepting a tissue treatment plan for the tissue to be treated, said treatment plan specifying a number and spacing of a plurality of treatment seeds for each of a plurality of respective said treatment seed strands that includes a distal end and a proximal end, where the distal end is intended to be implanted prior to the proximal end; and creating the plurality of treatment stranding, including providing a custom distal end spacing on each of the plurality of treatment seed stands to thereby enable the treatment seeds located adjacent to the distal ends of the treatment seed strands to be properly spaced relative to the distal ends of the treatment seed strands, in accordance with the treatment plan, when the distal ends of the plurality of the treatment seed strands are implanted to the same deoth using needles that are inserted to the same depth;

wherein the custom distal end spacings of the at least two of the plurality treatment seed strands have different lengths.

8. The method of claim 7, wherein:

said accepting step includes accepting said tissue treatment plan created with the use of a computer program.

9. The method of claim 7, wherein:

said accepting step includes accepting a treatment plan that specifies a number of radioactive seeds and a desired spacing between each pair of the radioactive seeds; and wherein said creating step includes creating the plurality of treatment seed strands to the specified desired spacing.

10. The method of claim 7, wherein:

said creating step includes positioning radioactive seeds in a mold at desired spacings and introducing a material to mold with the plurality of radioactive seeds in place in the desired spacings.

11. The method of claim 10, wherein the material is bio-absorbable.

12. The method of claim 10, wherein the material is a polymer.

13. The method of claim 10, wherein:

said accepting step includes using the tissue treatment plan wherein the tissue treatment plan is created using an imaging device.

14. A therapeutic kit comprising:

a plurality of seed strands configured to be implanted into a patient to the same depth using needles that are inserted into the patient to the same depth, each having a length with a distal end;

a plurality of seeds provided along the length of each of the seed strands at spaced intervals without the use of pre-fabricated spacers; and custom end spacings according to a treatment plan provided between the seed located adjacent to the distal end of each of said seed strands and the distal end of each said seed strand, said custom end spacings created without use of pre-fabricated spacers;

wherein the custom end spacings cause the seeds located adjacent to the distal ends of the seed strands to be properly spaced relative to the distal ends of the seed strands, according to the treatment plan, when the distal ends of the plurality of seed strands are implanted to the same depth using needles inserted to the same depth; and wherein the custom end spacings of at least two of said plurality of seed strands have different lengths.

15. A prescription method to create a treatment strand, the method comprising:

accepting a tissue treatment plan forte tissue to be treated, which treatment plan specifies a number and spacing of treatment seeds to be provided in the treatment plan; and creating a treatment strand that includes a custom distal end spacing that causes the treatment seed located adjacent to a distal end of the treatment strand to be properly spaced relative to the distal end of the treatment strand, according to the plan when the distal end of the treatment strand is implanted into a patient to a predefined depth using a needle that is inserted into the patient to the predefined depth.

16. A method of treating a patient with a plurality of treatment strands wherein each of said plurality of treatment stands has a plurality of spaced seeds and custom end spacings between a distal end seed in the strand and a distal end of the seed strand, the method comprising the steps of:

implanting a first strand at a desired location at a depth;

implanting the remainder of the plurality of seed strands at a plurality of respective desired locations to the depth of the first strand and wherein the custom end spacings of at least two of said plurality of seed strands have different lengths.

17. The method of claim 16 further comprising selecting at least two treatment seed strands that have custom end spacings of different lengths.

18. A prescription method to create a treatment seed strand, the method comprising:

accepting a tissue treatment plan for the tissue to be treated, said treatment plan specifying a number and spacing of a plurality of treatment seeds for each of a plurality of respective treatment seed strands;

creating the plurality of treatment seed strands from a material without using pre-fabricated spacers; and providing a custom distal end spacing on each of the plurality of treatment seed strands without using pre-fabricated spacers;

wherein the custom distal end spacings cause the treatment seeds located adjacent to distal ends of the treatment seed strands to be properly spaced relative to the distal ends of the treatment seed strands, according to the treatment plan, when the distal ends of the plurality of treatment seed strands are implanted to the same depth using needles inserted to the same depth; and wherein the custom distal end spacings of at least two of said plurality of seed strands have different lengths.

19. A prescription method to create a treatment seed strand, the method comprising the steps of:

accepting a tissue treatment plan for the tissue to be treated, said treatment plan specifying a number and spacing of a plurality of treatment seeds for each of a plurality of respective treatment seed strands; and creating the plurality of treatment seed strands from a material without using pre-fabricated spacers, such that each of the plurality of treatment seed strands includes a custom distal and spacing determined by the treatment plan; wherein the custom distal end spacings cause the treatment seeds located adjacent to distal ends of the treatment strands to be properly spaced relative to the distal end of the treatment strand;

wherein the custom distal end spacing on each of the plurality of treatment seed strands allows a health care professional to implant each of the plurality of treatment seed strands to a uniform depth in the tissue to be treated; and wherein the custom distal end spacing on at least two of said plurality of treatment seed strands have different lengths.

20. A method of treating a patient with a plurality of treatment strands wherein each of said plurality of treatment strands has a plurality of seeds and a custom end spacing between a distal end seed of the treatment strand and a distal end of the treatment strand, said custom end spacing set without using pre-fabricated spacers, the method comprising the steps of:

implanting a first treatment strand at a desired location such that the distal end of the first treatment strand is implanted at a depth; and implanting the remainder of the plurality of treatment strands at a plurality of respective desired locations with the distal ends of the plurality of the treatment strands implanted to the same depth of the first strand, wherein the distal end seed of at least two of said plurality of treatment strands are implanted to different depths due to the respective custom end spacing of the at least two treatment strands having different lengths.

21. A prescription method to create a treatment strand, the method comprising the steps of:

accepting a tissue treatment plan for the tissue to be treated, which treatment plan specifies a number and spacing of treatment seeds to be provided in each of a plurality of treatment strands;

creating the plurality of treatment strands according to said tissue treatment plan by positioning treatment seeds in a mold and introducing into the mold a material to mold the treatment seeds in place; and wherein at least two of the plurality of treatment seeds have a custom distal end spacing between the end of each treatment strand and the adjacent treatment seed;

wherein the custom distal end spacings cause the treatment seeds located adjacent to distal ends of the at least two of the treatment strands to be properly spaced relative to the distal ends of the treatment strands, according to the treatment plan, when the distal ends of the at least two of the treatment strands are implanted to the same depth using needles inserted to the same depth; and wherein the custom distal end spacings of the at least two of the treatment strands have different lengths.

22. The method of claim 19, wherein the material introduced into the mold is bio-absorbable.

23. The method of claim 21 wherein the material introduced into the mold is a polymer.

24. A therapeutic kit comprising:

a plurality of seed strands configured to be implanted into a patient to the same depth using needles that are inserted into the patient to the same depth, each having a length with a distal end;

a plurality of seeds provided along the length of each of the seeds strands; and custom end spacings according to a treatment plan provided between the seed located adjacent to the distal end of each of said seed strands and the distal end of each said seed strand, wherein the custom end spacings cause the seeds located adjacent to the distal ends of the seed strands to be properly spaced relative to the distal ends of the seed strands, according to the treatment plan, when the distal ends of the plurality of seed strands are implanted to the same depth using needles inserted to the same depth; and wherein the custom end spacings of at least two of said plurality of seed strands have different lengths.

* * * * *

UNITED STATES PATENT AND TRADEMARK OFFICE
CERTIFICATE OF CORRECTION

PATENT NO. : 6,997,862 B2  
APPLICATION NO. : 10/619928  
DATED : February 14, 2006  
INVENTOR(S) : Richard A. Terwilliger and Gary A. Lamoureux It is certified that error appears in the above-identified patent and that said Letters Patent is hereby corrected as shown below:

On The Title Page  
At item (73), replace "IdeaMatrix, Inc., Estes Park, CO (US)" with --Worldwide Medical Technologies, L.L.C. Oxford, CT (US) (part interest)

IdeaMatrix, Inc., Estes Park, CO (US) (part interest)--.

At column 13, line 20, replace "deoth" with --depth--;

At column 14, line 8, replace "forte" with --for the--.

Signed and Sealed this

Twelfth Day of September, 2006

JON W. DUDAS  
*Director of the United States Patent and Trademark Office*